United States Patent
Shi et al.

(10) Patent No.: US 10,555,880 B2
(45) Date of Patent: Feb. 11, 2020

(54) SODIUM ZINC ALGINATE STRUCTURANT AND METHODS FOR MAKING AND USING THE SAME

(71) Applicant: Colgate-Palmolive Company, New York, NY (US)

(72) Inventors: Manying Shi, Guangzhou (CN); Yun Xu, Langhorne, PA (US); Xiaojing Lu, Guangzhou (CN); Yuan Wu, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 44 days.

(21) Appl. No.: 16/062,163

(22) PCT Filed: Dec. 18, 2015

(86) PCT No.: PCT/CN2015/097859
§ 371 (c)(1),
(2) Date: Jun. 14, 2018

(87) PCT Pub. No.: WO2017/101098
PCT Pub. Date: Jun. 22, 2017

(65) Prior Publication Data
US 2018/0360710 A1    Dec. 20, 2018

(51) Int. Cl.
*A61K 6/00* (2006.01)
*A61K 8/27* (2006.01)
*A61Q 11/00* (2006.01)
*A61K 8/73* (2006.01)
*A61K 8/362* (2006.01)

(52) U.S. Cl.
CPC .............. *A61K 8/27* (2013.01); *A61K 8/362* (2013.01); *A61K 8/733* (2013.01); *A61Q 11/00* (2013.01); *A61K 2800/48* (2013.01)

(58) Field of Classification Search
None
See application file for complete search history.

(56) References Cited

U.S. PATENT DOCUMENTS

| | | |
|---|---|---|
| 4,022,880 A | 5/1977 | Vinson et al. |
| 4,100,269 A | 7/1978 | Pader |
| 4,775,525 A | 10/1988 | Pera |
| 4,992,259 A | 2/1991 | Schiraldi et al. |
| 5,438,076 A | 8/1995 | Friedman et al. |
| 9,095,530 B2 | 8/2015 | Won et al. |
| 2002/0155281 A1 | 10/2002 | Lang et al. |
| 2009/0142735 A1 | 6/2009 | Takushige et al. |
| 2011/0033511 A1 | 2/2011 | Pisula et al. |
| 2013/0251645 A1 | 9/2013 | Won et al. |
| 2013/0272970 A1 | 10/2013 | Pimenta et al. |
| 2015/0238395 A1 | 8/2015 | Plata et al. |
| 2016/0346185 A1 | 12/2016 | Lu |

FOREIGN PATENT DOCUMENTS

| | | |
|---|---|---|
| CN | 102204874 A | * 10/2011 |
| CN | 102204874 | 6/2012 |
| EP | 0045493 | 2/1982 |
| EP | 0747037 | 12/1996 |
| KR | 20130083556 | 7/2013 |
| WO | WO 90/015592 | 12/1990 |
| WO | 2011/092835 | 8/2011 |
| WO | 2015/109511 | 7/2015 |

OTHER PUBLICATIONS

Corresponding International Search Report and Written Opinion for Application No. PCT/CN2015/097859, dated Apr. 28, 2016. WO.

* cited by examiner

*Primary Examiner* — Susan T Tran

(57) ABSTRACT

Disclosed is a method of making a sodium zinc alginate structurant that can include combining a sodium alginate, a zinc compound, and a liquid media, and mixing to a desired viscosity. Further disclosed is a method of making an oral care composition that can include combining a sodium zinc alginate structurant with one or more agents, and mixing.

4 Claims, No Drawings

SODIUM ZINC ALGINATE STRUCTURANT AND METHODS FOR MAKING AND USING THE SAME

BACKGROUND

Alginate gum is a natural gum derived from seaweed. Alginate gum is an effective gelling and thickening agent and has been used in the food and pharmaceutical industries. One such commonly used alginate gum is sodium alginate. However, there are drawbacks to using sodium alginate in oral care compositions, such as toothpastes. Gels made from sodium alginate often lack the rheological and structural properties necessary to make striped toothpaste. Also, sodium alginate structurants have drawbacks in that their resulting toothpastes do not have the necessary flow characteristics and/or lack a clear appearance in an aqueous solution, which is demanded by the consumer.

There is a desire, therefore, to develop an improved sodium alginate structurant formulation and method of forming the same that has the rheological and structural properties necessary to make striped toothpastes, and yet still have continuous flow under an applied shear stress, and also have a clear, colorless appearance when in an aqueous solution.

BRIEF SUMMARY

A sodium zinc alginate structurant and methods for making and using the same are provided. In at least one specific embodiment, a method of making a sodium zinc alginate structurant can include combining one or more sodium alginates, one or more zinc compounds, and one or more liquid media, and mixing the one or more sodium alginates, the one or more zinc compounds, and the one or more liquid media to make a sodium zinc alginate structurant.

In at least one specific embodiment, a method of making an oral care composition can include combining one or more sodium alginates, one or more zinc compounds, and one or more liquid media; mixing the one or more sodium alginates, the one or more zinc compounds; and the one or more liquid media to make a sodium zinc alginate structurant; combining the sodium zinc alginate structurant with one or more agents; and mixing the sodium zinc alginate structurant with one or more agents to make an oral care composition.

In at least one specific embodiment, a method for using an oral care composition can include contacting an applicator to an oral care composition, wherein the oral care composition comprises a sodium zinc alginate structurant, and contacting the oral care composition to a tooth using the applicator.

DETAILED DESCRIPTION

It has been found that a sodium zinc alginate structurant can be made by mixing one or more sodium alginates, one or more zinc compounds, and one or more liquid media. The sodium zinc alginate structurant can be used in making oral care compositions, such as toothpaste. The rheological properties of the sodium zinc alginate structurant can be adjusted by the specific ratios of the zinc compounds to the sodium of the sodium alginate. Furthermore, this zinc-containing structurant shows significant antibacterial efficacy as demonstrated by in vitro Planktonic Resazurin Assay test.

By using the sodium zinc alginate structurant as a rheology modifier, oral care compositions can have a clear and/or colorless appearance and desirable fluidity. It has been shown that the sodium zinc alginate at certain sodium-to-zinc ratios can provide the required body and/or viscosity and standup stripe quality for oral care compositions. Additionally, as mentioned above, antibacterial studies showed that the toothpaste compositions that included the sodium zinc alginate structurant exhibited strong antibacterial properties.

Without wanting to be bound by theory, it is believed that the one or more zinc compounds can crosslink the one or more sodium alginates, increasing its molecular weight and viscosity. The sodium zinc alginate structurant can include a three-dimensionally cross-linked network. It is postulated that the zinc ions ($Zn^{2+}$) can replace the sodium ions ($Na^+$) coordinated with the carboxyl groups of the sodium alginate to convert a 2-dimentional structure into a 3-dimentional structure via the divalent ions crosslinking of the two polymer chains. The degree of crosslinking, and thus the viscosity of the resulting product, can be modulated by the amount of zinc compounds that are added to the sodium alginates. The solubility and particle dimensions of the sodium zinc alginate structurant can be important characteristics for the elastic properties and firmness for their use in an oral care composition.

Method of Making Sodium Zinc Alginate Structurant

The one or more zinc compounds, the one or more sodium alginates, and the one or more liquid media can be combined simultaneously or sequentially, and accompanied by continuous or intermittent mixing or agitation until a desired viscosity is achieved. For example, a desired quantity of one or more zinc compounds, one or more sodium alginates, and one or more liquid media can be combined together at the same time or can be combined sequentially under continuous mixing or agitation.

Zinc Compounds

The zinc compounds can include, but are not limited to: zinc chloride, zinc citrate, zinc oxide, zinc lactate, and any mixture thereof. The sodium zinc alginate structurant can include one or more zinc compounds from a low of about 0.001 wt %, about 0.1 wt %, about 1 wt %, or about 2 wt % to a high of about 6 wt %, about 9 wt %, about 12 wt %, or about 20 wt %, based on the total weight of the one or more zinc compounds, the one or more sodium alginate, and the one or more liquid media. For example, the sodium zinc alginate structurant can include one or more zinc compounds from about 0.002 wt % to about 0.02 wt %, about 0.2 wt % to about 1 wt %, about 0.4 wt % to about 1.5 wt %, about 1.1 wt % to about 4.2 wt %, about 3.7 wt % to about 5.9 wt %, about 4.7 wt % to about 12 wt %, about 11 wt % to about 23 wt %, or about 7 wt % to about 19 wt %, based on the total weight of the one or more zinc compounds, the one or more sodium alginate, and the one or more liquid media.

If more than one zinc compound is present in the sodium zinc alginate structurant, the zinc compounds can be mixed in any ratio to make the sodium zinc alginate structurant. For example, if two zinc compounds are present in the sodium zinc alginate structurant the mixing ratio of the two zinc compounds can be in a weight ratio of about 99:1, about 90:10, about 80:20, about 70:30, about 60:40, about 50:50, about 40:60, about 30:70, about 20:80, about 10:90, or about 1:99. In another example, the mixing ratio of the two zinc compounds can be in a weight ratio of about 0.05:1, about 1:1, about 1:2, about 2:3, about 3:7, or about 1:4.

Sodium Alginate

Sodium alginate is a polymer derived from seaweeds and algae. Sodium alginate is the sodium salt of alginic acid. Alginic acid and its salt forms are linear block copolymers with homopolymeric blocks of (1-4)-linked β-D-mannuronate residues and α-L-guluronate residues covalently bonded together in different blocks. The monomers can appear in homopolymeric blocks of consecutive β-D-mannuronate residues, consecutive α-L-guluronate residues or alternating β-D-mannuronate and α-L-guluronate residues.

The sodium zinc alginate structurant can include one or more sodium alginates from a low of about 0.001 wt %, about 0.1 wt %, about 1 wt %, or about 2 wt % to a high of about 6 wt %, about 9 wt %, about 12 wt %, or about 20 wt %, based on the total weight of the one or more zinc compounds, the one or more sodium alginate, and the one or more liquid media. For example, the sodium zinc alginate structurant can include one or more sodium alginates from about 0.002 wt % to about 0.02 wt %, about 0.2 wt % to about 1 wt %, about 0.4 wt % to about 1.5 wt %, about 1.1 wt % to about 4.2 wt %, about 3.7 wt % to about 5.9 wt %, about 4.7 wt % to about 12 wt %, about 11 wt % to about 23 wt %, about 7 wt % to about 19 wt %, based on the total weight of the one or more zinc compounds, the one or more sodium alginate, and the one or more liquid media.

The weight ratio of the one or more sodium alginates to the one or more zinc compounds can be adjusted to provide the desired rheological properties for the sodium zinc alginate structurant and the oral care compositions made therefrom. The one or more sodium alginates and the one or more zinc compounds can be mixed in any ratio to make the sodium zinc alginate structurant. For example, the mixing ratio of the one or more sodium alginate and the one or more zinc compounds can be in a weight ratio of about 99:1, about 90:10, about 80:20, about 70:30, about 60:40, about 50:50, about 40:60, about 30:70, about 20:80, about 10:90, or about 1:99. In another example, the mixing ratio of the one or more sodium alginate and the one or more zinc compounds can be in a weight ratio of about 0.03:1, about 0.04:1, about 0.05:1, about 0.06:1, or about 0.07:1.

The sodium zinc alginate structurant can include one or more sodium alginates and the one or more zinc compounds from a low of about 0.001 wt %, about 0.1 wt %, about 1 wt %, or about 2 wt % to a high of about 6 wt %, about 9 wt %, about 12 wt %, or about 20 wt %, based on the total weight of the one or more zinc compounds, the one or more sodium alginate, and the one or more liquid media. For example, sodium zinc alginate structurant can include one or more sodium alginates and the one or more zinc compounds from about 0.002 wt % to about 0.02 wt %, about 0.2 wt % to about 1 wt %, about 0.4 wt % to about 1.5 wt %, about 1.1 wt % to about 4.2 wt %, about 3.7 wt % to about 5.9 wt %, about 4.7 wt % to about 12 wt %, about 11 wt % to about 16 wt %, about 7 wt % to about 19 wt %, based on the total weight of the one or more zinc compounds, the one or more sodium alginate, and the one or more liquid media

Liquid Media

The liquid media used to make the sodium zinc alginate structurant can include, but are not limited to: water, sorbitol, glycerin, methanol, ethanol, ethyl acetate, acetone, isopropanol, benzyl alcohol, and mixtures thereof. The sodium zinc alginate structurant can have a liquid media content from a low of about 1 wt %, about 10 wt %, about 20 wt %, or about 40 wt % to a high of about 85 wt %, about 85 wt %, about 95 wt %, or about 99.5 wt %, based on the total weight of the one or more sodium alginates, the one or more zinc compounds, and the one or more liquid media. For example, the sodium zinc alginate structurant can have a liquid media content of about 99 wt % or less, about 95 wt % or less, about 90 wt % or less, about 85 wt % or less, about 80 wt % or less, or about 75 wt % or less, based on the total weight of the one or more sodium alginate, the one or more zinc compounds, and the one or more liquid media. In another example, the sodium zinc alginate structurant can have a liquid media content of about 15 wt % to about 25 wt %, about 20 wt % to about 30 wt %, about 20 wt % to about 59 wt %, about 25 wt % to about 35 wt %, about 47 wt % to about 80 wt %, about 73 wt % to about 93 wt %, about 80 wt % to about 99 wt %, about 90 wt % to about 98 wt %, or about 95 wt % to about 99 wt %, based on the total weight of the one or more sodium alginates, the one or more zinc compounds, and the one or more liquid media.

The sodium zinc alginate structurant can be a solid, liquid, dispersion, emulsion, suspension, slurry, gel, or any mixture thereof. The viscosity of the sodium zinc alginate structurant can vary widely. For example, the viscosity of the sodium zinc alginate structurant can be from a low of about 1 centipoise ("cP"), about 100 cP, about 250 cP, about 500 cP, or about 700 cP to a high of about 1,000 cP, about 3,250 cP, about 4,500 cP, about 5,000 cP, or about 10,000 cP at a temperature of about 25° C. In another example, the sodium zinc alginate structurant can have a viscosity from about 10 cP to about 125 cP, about 20 cP to about 75 cP, about 75 cP to about 125 cP, about 260 cP to about 460 cP, about 725 cP to about 1,100 cP, about 1,200 cP to about 2,000 cP, about 4,100 cP to about 8,600 cP, about 8,600 cP to about 9,200 cP, or about 7,900 cP to about 9,990 cP at a temperature of about 25° C. In another example, the sodium zinc alginate structurant can have a viscosity from about 1 cP to about 450 cP, about 450 cP to about 1,205, about 6,250 cP to about 7,550 cP, about 6,550 cP to about 8,250 cP, about 7,250 cP to about 9,100 cP, about 8,100 cP to about 9,600 cP, or about 6,600 cP to about 8,200 cP at a temperature of about 25° C. The viscosity can be measured using a viscometer.

Method of Making Oral Care Compositions

The sodium zinc alginate structurant can be used to make oral care compositions such as toothpastes, which includes tooth-cleaning gels and striped tooth-cleaning products. The oral care composition can include one or more agents. The one or more agents that can be included in the oral care composition can include, but are not limited to: humectants, flavorants, colorants, acids, bases, antibacterial agents, solvents or diluents, bicarbonate salts, surfactants, foam modulators, abrasives, sweeteners, tooth whiteners, saliva stimulating, antimicrobial agents, antioxidants, anti-caries agents, fluoride compounds, tartar control agents, additional structurants, and mixtures thereof.

The one or more agents can be combined simultaneously or sequentially, and accompanied by continuous or intermittent mixing or agitation. For example, a desired quantity of sodium zinc alginate structurant and a suitable amount of the one or more agents can be combined together at the same time or one or more of agents can be combined sequentially under continuous mixing or agitation.

The humectants can include, but are not limited to, sorbitol, polyethylene glycol, or any mixture thereof. A humectant can be present in the oral care composition from a low of a low of about 1 wt %, about 5 wt %, about 7 wt %, or about 10 wt % to a high of about 50 wt %, about 60 wt %, about 72 wt %, or about 80 wt %, based on the total weight of the sodium zinc alginate structurant and the one or more agents. For example, the humectants can be present in the oral care composition from about 1 wt % to about 12 wt %, about 20 wt % to about 40 wt %, about 39 wt % to about 55 wt %, about 41 wt % to about 62 wt %, about 47 wt % to about 81 wt %, about 55 wt % to about 85 wt %, about 60 wt % to about 75 wt %, 52 wt % to about 66 wt %, or about 61 wt % to about 79 wt %, based on the total weight of the sodium zinc alginate structurant and the one or more agents.

The flavoring agents can include, but are not limited to: vanillin, sage, marjoram, parsley oil, spearmint oil, cinnamon, wintergreen oil (methylsalicylate), peppermint oil; clove oil; bay oil; anise oil; citrus oils; fruit oils and essences, such as those derived from lemon, orange, lime, grapefruit, apricot, banana, grape, apple, strawberry, cherry, pineapple, and the like; bean- and nut-derived flavors, such as coffee, cocoa, cola, peanut, almond, and the like; sassafras; clove; sage; eucalyptus; marjoram; menthol; carvone; anethole; raspberry 73562; cyclamates; acesulfane-K; thaumatin; neohisperidin dihydrochalcone; D-tryptophan, ammoniated glycyrrhizin; and mixtures thereof. Also encompassed within flavorants herein are ingredients that provide fragrance and/or other sensory effects in the mouth, such as cooling or warming effects. Such agents can include, but are not limited to: menthol; menthyl acetate; menthyl lactate; camphor; eucalyptus oil; eucalyptol; anethole; eugenol; cassia; oxanone; α-irisone; propenyl guaiethol; thymol; linalool; benzaldehyde; cinnamaldehyde; N-ethyl-p-menthan-3-carboxamine; N,2,3-trimethyl-2-isopropylbutanamide, 3-(1-menthoxy)-propane-1,2-diol; cinnamaldehyde glycerol acetal, menthone glycerol acetal (MGA) and the like.

The flavorants can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the flavorants can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The sweeteners can include, but are not limited to: saccharin, xylitol, perillartien, sucrose, glucose, sucralose, dextrose, levulose, lactose, thaumatin, neohisperidin dihydrochalcone, mannitol, sorbitol, fructose, maltose, xylitol, thaumatin, aspartame, dihydroehalcones, xylitol, acesulfame, cyclamate salts, and mixtures thereof. The sweeteners can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the sweetener can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

Colorants can include, but are not limited to: pigments, dyes, lakes and agents imparting a particular luster or reflectivity, such as pearling agents. The colorants can include but are not limited to: talc; mica; magnesium carbonate; calcium carbonate; magnesium silicate; magnesium aluminum silicate; silica; titanium dioxide; iron oxides; ferric ammonium ferrocyanide, manganese violet; ultramarine; titaniated mica; bismuth oxychloride; and the like. Commercially available colorants can be used in the oral care composition disclosed herein. Such commercially available colorants can include, but are not limited to: D&C yellow #10, Blue #15, manufactured by BASF of Ludwigshafen, Germany.

The colorants can be present in the oral care composition from a low of about 0.0001 wt %, about 0.001 wt %, 0.01 wt %, or about 0.1 wt %, to a high of about 3 wt %, about 4 wt %, or about 4 wt %, based on the total weight of the sodium zinc alginate structurant and the one or more agents. For example, the colorants can be present in the oral care composition from a low from about 0.0001 wt % to about 0.01 wt %, about 0.001 wt % to about 0.1 wt %, about 0.1 wt % to about 0.9 wt %, about 0.8 wt % to about 1.2 wt %, about 0.7 wt % to about 1.9 wt %, about 1.7 wt % to about 2.9 wt %, about 1.1 wt % to about 3.9 wt %, about 2.7 wt % to about 3.9 wt %, about 1.7 wt % to about 4.9 wt %, based on the total weight of the sodium zinc alginate structurant and the one or more agents.

The anti-microbial agents can include, but are not limited: benzoic acid, sodium benzoate, potassium benzoate, boric acid, betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetlpyridinium fluoride, cetylpyridinium chloride, cetypyridinium bromide, triclosan, and mixtures thereof.

The anti-microbial agents can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the anti-microbial agents can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The anti-sensitivity agents can include, but are not limited: potassium salts such as potassium nitrate, potassium bicarbonate, potassium chloride, potassium citrate, and potassium oxalate; capsaicin; eugenol; strontium salts; zinc salts; chloride salts; and mixtures thereof. The oral care composition may treat hyper-sensitivity by blocking dentin tubules.

The anti-sensitivity agents can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the anti-sensitivity agents can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The tooth whitening agents can include, but are not limited to: peroxides, such as hydroperoxides, hydrogen peroxide, lithium peroxide, potassium peroxide, sodium peroxide, magnesium peroxide, calcium peroxide, barium peroxide, peroxy acids; metal chlorites, such as calcium chlorite, barium chlorite, magnesium chlorite, lithium chlorite, sodium chlorite, and potassium chlorite; persulfates; sodium perborate; and mixtures thereof.

The tooth whitening agents can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the tooth whitening agents can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

Abrasives can include, but are not limited to: aluminum oxide, aluminum silicate, calcined alumina, bentonite, silica, insoluble phosphates, calcium carbonate, and mixtures thereof. Insoluble phosphates can include, but are not limited to: dicalcium orthophosphate dihydrate, calcium pyrophosphate, calcium pyrophosphate, tricalcium phosphate, calcium polymetaphosphate, sodium polymetaphosphate, and mixtures thereof. Commercially available abrasives can be used in the oral care composition disclosed herein. Such commercially available abrasives can include, but are not limited to: ZEODENT® 105, 114, and 165, manufactured by J.M. Huber Corporation of Edison, N.J., and SYLODENT® 783, manufactured by W.R. Grace & Company of Columbia, Md.

The abrasives can be present in the oral care composition from a low of about 1 wt %, about 2 wt %, or about 4 wt %, to a high of about 20 wt %, about 25 wt %, or about 35 wt %, based on the total weight of the sodium zinc alginate structurant and the one or more agents. For example, the abrasives can be present in the oral care composition from a low from about 1 wt % to about 2 wt %, about 1.2 wt % to about 3 wt %, about 1.7 wt % to about 3.5 wt %, about 1.1 wt % to about 4.2 wt %, about 3.7 wt % to about 5.9 wt %, about 4.7 wt % to about 12 wt %, about 11 wt % to about 23 wt %, about 7 wt % to about 19 wt %, about 17 wt % to about 27 wt %, about 20 wt % to about 35 wt %, based on the total weight of the sodium zinc alginate structurant and the one or more agents.

The surfactants can be anionic, cationic, zwitterionic, nonionic surfactants, and mixtures thereof. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate ("SLS"), sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate.

The surfactants can be present in the oral care composition from a low of about 1 wt %, about 2 wt %, or about 4 wt %, to a high of about 20 wt %, about 25 wt %, or about 35 wt %, based on the total weight of the sodium zinc alginate structurant and the one or more agents. For example, the surfactants can be present in the oral care composition from a low from about 1 wt % to about 2 wt %, about 1.2 wt % to about 3 wt %, about 1.7 wt % to about 3.5 wt %, about 1.1 wt % to about 4.2 wt %, about 3.7 wt % to about 5.9 wt %, about 4.7 wt % to about 12 wt %, about 11 wt % to about 23 wt %, about 7 wt % to about 19 wt %, about 17 wt % to about 27 wt %, about 20 wt % to about 35 wt %, based on the total weight of the sodium zinc alginate structurant and the one or more agents.

Fluoride compounds can include, but are not limited to: sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides.

The oral care composition can include one or more fluoride compounds from a low of about 0.1 wt %, about 1 wt %, about 2 wt %, or about 3 wt % to a high of about 6 wt %, about 9 wt %, about 12 wt %, or about 20 wt %, based on the total weight of the sodium zinc alginate structurant and the one or more agents. For example, the oral care composition can include one or more fluoride compounds from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the sodium zinc alginate structurant and the one or more agents.

In another aspect, the fluoride compounds can dissociate to provide fluoride ions in a concentration from a low of about 5,000 ppm, about 7,000 ppm, about 9,000 ppm, or about 10,000 ppm to a high of about 20,000 ppm, about 30,000 ppm, 40,000, or about 50,000 ppm. For example, the one or more fluoride compounds can dissociate to provide fluoride ions in a concentration from about 5,000 ppm to about 7,000 ppm, about 6,000 ppm to about 12,000 ppm, about 11,000 ppm to about 21,000 ppm, about 19,000 ppm to about 27,000 ppm, about 26,000 ppm to about 37,000 ppm, about 25,000 ppm to about 37,000 ppm, about 28,000 ppm to about 50,000 ppm. In order to provide such a concentration in the desired ppm range, the exact weight percentage of the one or more fluoride compounds in the oral care composition can vary widely, depending upon the stoichiometric ratio of the fluoride within the compound.

The tartar control agents can include: phosphates and polyphosphates (for example pyrophosphates); polyaminopropanesulfonic acid (AMPS); polyolefin sulfonates; polyolefin phosphates; diphosphonates, such as azacycloalkane-2,2-diphosphonates (e.g., azacycloheptane-2,2-diphosphonic acid); N-methyl azacyclopentane-2,3- diphosphonic acid; ethane-1-hydroxy-1,1-diphosphonic acid (EHDP), and ethane-1-amino-1,1-diphosphonate, phosphonoalkane carboxylic acids, and the like. Useful inorganic phosphate and polyphosphate salts include monobasic, dibasic and tribasic sodium phosphates, such as sodium tripolyphosphate, tetrapolyphosphate, mono-, di-, tri- and tetrasodium pyrophosphates, sodium trimetaphosphate, sodium hexametaphosphate, and mixtures thereof.

The tartar control agents can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the tartar control agents can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The bicarbonate salts can impart a "clean feel" to teeth and gums due to effervescence and release of carbon dioxide. The bicarbonate salts can including, but are not limited to: alkali metal bicarbonates, such as sodium and potassium bicarbonates, ammonium bicarbonate and the like. The bicarbonate salts can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the bicarbonate salts can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The antibacterial agents can include, but are not limited to: chlorhexidine; triclosan; quaternary ammonium compounds (e.g., benzalkonium chloride); parabens, such as methylparaben or propylparaben. The antibacterial agents can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the antibacterial agents can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents The anti-sensitivity agents can include, but are not limited to: potassium salts, such as potassium nitrate, potassium bicarbonate, potassium chloride, potassium citrate, and potassium oxalate; capsaicin; eugenol; strontium salts; zinc salts; chloride salts and combinations thereof. The oral care composition can include one or more anti-sensitivity agents from a low of about 0.1 wt %, about 1 wt %, about 2 wt %, or about 3 wt % to a high of about 6 wt %, about 9 wt %, about 12 wt %, or about 20 wt %, based on the total weight of the sodium zinc alginate structurant and the one or more agents. For example, the oral care composition can include one or more anti-sensitivity agents from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the sodium zinc alginate structurant and the one or more agents.

The antioxidants can include, but are not limited to: butylated hydroxyanisole ("BHA"), butylated hydroxytoluene ("BHT"), vitamin A, carotenoids, vitamin E, flavonoids, polyphenols, ascorbic acid, herbal antioxidants, chlorophyll, melatonin, and mixtures thereof. The oral care composition can include one or more antioxidants from a low of about 0.1 wt %, about 1 wt %, about 2 wt %, or about 3 wt % to a high of about 6 wt %, about 9 wt %, about 12 wt %, or about 20 wt %, based on the total weight of the sodium zinc alginate structurant and the one or more agents. For example, the oral care composition can include one or more antioxidants from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the sodium zinc alginate structurant and the one or more agents.

The oral care composition can include additional structurants besides and in addition to the zinc alginate structurant. The additional structurants can include, but are not limited to, a silica thickener. The oral care composition can include additional structurants from a low of about 0.1 wt %, about 1 wt %, about 2 wt %, or about 3 wt % to a high of about 6 wt %, about 9 wt %, about 12 wt %, or about 20 wt %, based on the total weight of the sodium zinc alginate structurant and the one or more agents. For example, the oral care composition can include additional structurants from about 0.01 wt % to about 0.1 wt %, about 0.1 wt % to about 1 wt %, about 1 wt % to about 4 wt %, about 2 wt % to about 6 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the sodium zinc alginate structurant and the one or more agents.

The liquid media used to make the oral care composition can include, but are not limited to: water, methanol, ethanol, ethyl acetate, acetone, isopropanol, benzyl alcohol, and mixtures thereof. The liquid media used to make the sodium zinc alginate structurant can be the same or different than the liquid media used to make the oral care composition.

The oral care composition can have a liquid media content from a low of about 18 wt %, about 20 wt %, or about 25 wt % to a high of about 35 wt %, about 40 wt %, or about 59 wt %, based on the total weight of the one or more sodium alginate, the one or more zinc compounds, and the one or more liquid media. For example, the sodium zinc alginate structurant can have a liquid media content of about 59 wt % or less, about 45 wt % or less, about 40 wt % or less, about 35 wt % or less, about 30 wt % or less, or about 25 wt % or less, based on the total weight of the one or more sodium alginate, the one or more zinc compounds, and the one or more liquid media. In another example, the sodium zinc alginate structurant can have a liquid media content of about 15 wt % to about 25 wt %, about 20 wt % to about 30 wt %, about 20 wt % to about 59 wt %, about 25 wt % to about 35 wt %, about 27 wt % to about 40 wt %, about 33 wt % to about 43 wt %, about 37 wt % to about 49 wt %, about 45 wt % to about 56 wt %, or about 45 wt % to about 59 wt %, based on the total weight of the one or more sodium alginate, the one or more zinc compounds, and the one or more liquid media.

Acids and/or bases can be used to adjust the pH and/or buffer the oral care composition. The acids can include, but are not limited to: sodium carbonate, sodium bicarbonate, sodium dihydrogen phosphate, sodium hydrogen phosphate, trisodium phosphate, sodium hydroxide, sodium carbonate, citric acid, sodium citrate, and mixtures thereof. The bases can include, but are not limited to: sodium hydroxide, potassium hydroxide, and mixtures thereof. The oral care composition can have a pH from a low of 4.0 to a high of about pH 9.0. For example, the oral care composition can have pH from about 4.0 to about 5.0, about 4.5 to about 6.0, about 5.5 to about 6.5, about 6.0 to about 7.0, about 6.5 to about 8.0, or about 7.5 to about 9.0.

The acids and/or bases can be present in the oral care composition from a low of about 0.01 wt %, about 0.1 wt %, or about 1 wt %, to a high of about 4 wt %, about 5 wt %, or about 6 wt %, based on the total weight of the sodium zinc alginate structurant and the one or more agents. For example, the acids and/or bases can be present in the oral care composition from a low from about 0.01 wt % to about 1.2 wt %, about 0.04 wt % to about 0.9 wt %, about 0.7 wt % to about 1.5 wt %, about 1.1 wt % to about 2.2 wt %, about 0.7 wt % to about 1.9 wt %, about 1.7 wt % to about 2.9 wt %, about 1.1 wt % to about 3.9 wt %, about 2.7 wt % to about 4.9 wt %, about 1.7 wt % to about 5.9 wt %, based on the total weight of the sodium zinc alginate structurant and the one or more agents.

The oral care composition can be a solid, liquid, dispersion, emulsion, suspension, slurry, gel or any mixture thereof. The viscosity of the oral care compositions can vary widely. For example, the viscosity of the oral care composition can be from a low of about 1 centipoise ("cP"), about 1,000 cP, about 1,250 cP, about 20,000 cP, or about 30,000 cP to a high of about 500,000 cP, about 700,000 cP, about 800,000 cP, or about 900,000 cP at a temperature of about 25° C. For example, oral care composition can have a viscosity from about 1,500 cP to about 12,500 cP, about 12,000 cP to about 75,000 cP, about 25,000 cP to about 125,000 cP, about 160,000 cP to about 460,000 cP, about 55,000 cP to about 400,000 cP, about 350,000 cP to about 550,000 cP, about 150,000 cP to about 650,000 cP, or about 345,000 cP to about 700,000 cP at a temperature of about 25° C. In another example, the oral care composition can have a viscosity from about 245,000 cP to about 500,000 cP, about 445,000 cP to about 650,000 cP, or about 600,000 cP to about 900,000 cP at a temperature of about 25° C. The viscosity can be measured using a viscometer.

Further disclosed herein are methods of using the oral care composition. The oral care composition can be applied to the surface of a tooth to clean and/or inhibit dental caries. The oral care composition can be applied to a tooth by any means. An applicator, such as a brush or a dental tray, can be used to apply the composition. For example, the oral care composition can be applied by contacting a brush with the composition and then using the brush to contact the composition to the surface of a tooth. Or in other words, the oral care composition can be applied by a user brushing his or her teeth using a toothbrush.

EXAMPLES

In order to provide a better understanding of the foregoing discussion, the following non-limiting examples are offered. Although the examples can be directed to specific embodiments, they are not to be viewed as limiting the invention in any specific respect.

Dose Response Study of Vary $ZnCl_2$ Concentrations

A series of sodium zinc alginate structurants were prepared by combining sodium alginate ("SA") (0.14 g) with water (99.86 g, 99.83 g, 99.82 g, and 99.80 g) and $ZnCl_2$ (0 g, 0.03 g, 0.04 g, and 0.06 g), respectively, and mixing. In other words, the sodium to alginate concentration was held constant at 0.14 wt % for each of the sodium zinc alginate structurants, while the $ZnCl_2$ concentration was varied at 0 wt %, 0.03 wt %, 0.04 wt %, and 0.06 wt % with the balance being water. The viscosity was measured by using a viscometer. Table 1 shows the viscosity of the sodium zinc alginate structurants at the various $ZnCl_2$ concentrations.

TABLE 1

Dose Response Study with 0.14 wt % Sodium Alginate

| $ZnCl_2$ Level (wt %) | Viscosity (cPs) |
| --- | --- |
| 0.00 | 66 |
| 0.03 | 2320 |
| 0.04 | 1180 |
| 0.06 | 78 |

The structuring characteristic or power is not linear with the number of zinc ions in the formula. As shown, there is an optimal amount of zinc at which maximum viscosity is achieved. Beyond the optimal zinc concentration, the viscosity decreases with a continued increase of zinc. At a concentration of 0.14 wt % of sodium alginate, the viscosity of the baseline sodium alginate is 66 cP, without any zinc chloride. The viscosity increases as zinc chloride is added to form a sodium zinc alginate structurant, rising to 2,320 cP when 0.03 wt % zinc chloride is added. The viscosity decreases when more than 0.03 wt % zinc chloride concentration is added.

Zinc Compounds' Effects on Initial Viscosity, Thixotropic Profile, Antibacterial Efficacy and Formula Stability Toothpaste compositions made from sodium zinc alginate structurants containing four different zinc compounds and one mixture of zinc compounds were evaluated for their initial viscosity, thixotropic profile, and antibacterial efficacy. Table 2 shows the solubility, total zinc and soluble zinc of these zinc compounds at their use level.

TABLE 2

Solubility, Total Zinc and Soluble Zinc

| Test | Zinc Compounds | Solubility (g/100 g $H_2O$, 25° C.) | Use level in Formula | Total Zinc Conc. | Calculated Soluble Zinc |
| --- | --- | --- | --- | --- | --- |
| #1 | Zn Citrate | 3.6 | 2% | 0.68% | 0.28% |
| #2 | ZnO | 0.00016 | 1% | 0.80% | 0.000029% |
| #3 | Zn Citrate/ZnO mixture | 3.6/0.00016 | 0.5%/1% | 0.97% | 0.085% |
| #4 | $ZnCl_2$ | 408 | 1.5% | 0.72% | 0.72% |
| #5 | Zn Lactate | 5.5 | 2.6% | 0.69% | 0.33% |

Inventive toothpaste compositions (Ex. 1-5) and a comparative toothpaste composition (C1) were made. The inventive toothpaste compositions contained the sodium zinc alginate structurant, while the comparative toothpaste composition replaced the sodium zinc alginate structurant with magnesium aluminum silicate and adjusting the buffer system (i.e., 0.2 wt % NaHCO$_3$, 0.8 wt % Na$_2$CO$_3$) to stabilize the fluoride compound.

To make the inventive toothpaste compositions (Ex. 1-5), sodium alginate was dispersed in polyethylene glycol or water to make a slurry. The respective zinc compounds were combined with the slurry and mixed to make the sodium zinc alginate structurant. For the comparative toothpaste composition (C1), carboxymethyl cellulose ("CMC") and magnesium aluminum silicate were combined and mixed to make a comparative structurant. Sorbitol, sodium monofluorophosphate, sodium saccharin, carboxymethyl cellulose, and the colorants were added to the structurants and stirred for 10 minutes. Demineralized water was then added to the gel tank and stirred for 5 minutes. The temperature was increased to 45° C., and the mixture was stirred for 10 minutes. The mixture was transferred to a paste tank and deaerated for 2 minutes at full vacuum. Vacuum was set at −0.070 MPa with agitation/homogenous set at 75/1800 rpm, respectively. Silica was then added under vacuum at −0.070 MPa and agitation/homogenous of 75/1800 rpm, respectively. The mixture was stirred for 10 minutes to make a paste. The paste was inspected for white lumps. If lumps were present, the mixture was stirred for an additional 10 minutes at agitation/homogenous of 75/1800 rpm. The flavorant was added and the mixture was stirred for 5 minutes at 45° C. under vacuum. Sodium lauryl sulfate was added stirred for 5 minutes. The betaine was then added and stirred for 0.095 minutes under full vacuum until homogenous toothpaste composition was formed. The toothpaste compositions are shown in Table 3.

TABLE 3

Composition of the Formulas

| Ingredient | C1 Dosage, % | Ex. 1 Dosage, % | Ex. 2 Dosage, % | Ex. 3 Dosage, % | Ex. 4 Dosage, % | Ex. 5 Dosage, % |
|---|---|---|---|---|---|---|
| Sorbitol | 21.00 | 21.0 | 21.00 | 21.00 | 21.00 | 21.00 |
| Na Saccharin | 0.25 | 0.25 | 0.25 | 0.25 | 0.25 | 0.25 |
| MFP | 1.10 | 1.10 | 1.10 | 1.10 | 1.10 | 1.10 |
| CMC-TMS | 1.00 | 1.00 | 1.00 | 1.00 | 1.00 | 1.00 |
| Sodium Alginate | — | 0.06 | 0.06 | 0.06 | 0.06 | 0.06 |
| NaHCO$_3$ | 0.20 | 0.20 | 0.20 | 0.20 | 0.20 | 0.20 |
| Sodium Carbonate (Na$_2$CO$_3$) | 0.80 | 0.80 | 0.80 | 0.80 | 0.80 | 0.80 |
| Purified Water | 23.64 | 23.58 | 22.58 | 23.08 | 23.08 | 21.98 |
| NCC | 42.00 | 42.00 | 42.00 | 42.00 | 42.00 | 42.00 |
| ZeO 165 | 2.00 | 2.00 | 2.00 | 2.00 | 2.00 | 2.00 |
| Benzyl Alcohol | 0.30 | 0.30 | 0.30 | 0.30 | 0.30 | 0.30 |
| 35% Liquid SLS | 5.71 | 5.714 | 5.71 | 5.71 | 5.71 | 5.71 |
| Salt White Flavor | 1.00 | 1.00 | 1.00 | 1.00 | 1.00 | 1.00 |
| Magnesium Aluminum Silicate (MAS) | 1.00 | — | — | — | — | — |
| Zinc Citrate Trihydrate | — | — | 2.00 | 0.50 | — | — |
| ZnO | — | 1.00 | — | 1.00 | — | — |
| ZnCl$_2$ | — | — | — | — | 1.50 | — |
| Zn Lactate | — | — | — | — | — | 2.60 |
| Total | 100.00 | 100.00 | 100.00 | 100.00 | 100.00 | 100.00 |

Initial Viscosity

The initial viscosity is the viscosity measured right after the toothpaste composition is made. The initial viscosity is critical for gaining good stripe quality. For example, if the initial viscosity is too low, it cannot be striped. Table 4 shows the initial viscosity of the toothpaste compositions containing the four zinc compounds, the zinc citrate/zinc oxide mixture, and the control composition. All five of the inventive toothpaste compositions had desirable initial viscosity, and all five reached their viscosity plateau within a week. It is noteworthy that the least soluble zinc compound, i.e., the zinc oxide, gave a toothpaste composition with a comparable initial viscosity and one week viscosity. Although in theory, there are fewer free zinc ions that are in solution and can crosslink with sodium alginate to form a structurant with a higher viscosity.

TABLE 4

Initial Viscosity Study

| Test No. | Key Components in Formula (%) | | | | | Aging Viscosity (x10000 cps) | | | |
|---|---|---|---|---|---|---|---|---|---|
| | CMC | MAS | SA | Zinc | Thickening Silica | Initial | 1 h | 1 d | 1 wk |
| Ex. 1 | 1 | — | 0.06 | 2 wt % Zinc Citrate | 2 | 26.1 | 28.8 | 39.4 | 39.3 |
| Ex. 2 | 1 | — | 0.06 | 0.5 wt % Zinc Citrate, 1 wt % ZnO | 2 | 25.1 | 29.3 | 36.2 | 39.7 |
| Ex. 3 | 1 | — | 0.06 | 1.5 wt % ZnCl$_2$ | 2 | 25.5 | — | — | 50.6 |
| Ex. 4 | 1 | — | 0.06 | 2.6 wt % Zinc Lactate | 2 | 20.0 | 25.3 | 35.0 | 40.0 |
| Ex. 5 | 1 | — | 0.06 | 1 wt % ZnO | 2 | 22.4 | 25.8 | 34.9 | 41.1 |
| Comp. | 1 | 1 | — | — | 2 | 24.6 | — | 35.2 | 38.7 |

Thixotropic Profiling

A thixotropic profile can confirm whether a toothpaste composition with a good initial viscosity can provide a good-quality stripe in a finished product. Tables 5A and 5B show the thixotropic profiles of five of the toothpaste compositions having the sodium zinc alginate structurant and the comparative example. All the toothpaste compositions made with the sodium zinc alginate structurant were similar to the comparative, suggesting that they could be striped.

TABLE 5A

Thixotropic Profiles

| C1: 1 wt % CMC, 1 wt % MAS | | Ex. 1: 1 wt % CMC, 0.06 wt %, Sodium Alginate, 2 wt % Zinc Citrate | | Ex. 2: 1 wt % CMC, 0.06 wt % Sodium Alginate, 0.5 wt % Zinc Citrate, 1 wt % ZnO | |
|---|---|---|---|---|---|
| Shear rate (1/s) | Shear stress (Pa) | Shear rate (1/s) | Shear stress (Pa) | Shear rate (1/s) | Shear stress (Pa) |
| 0.5162 | 136 | 0.5139 | 116 | 0.4866 | 110.3 |
| 0.9928 | 277.9 | 0.9916 | 225.9 | 0.9444 | 217.5 |
| 1.446 | 401.5 | 1.444 | 326.4 | 1.463 | 332.9 |
| 1.881 | 461 | 1.88 | 382 | 1.894 | 385.7 |
| 2.378 | 473.1 | 2.377 | 405.7 | 2.397 | 408 |
| 2.869 | 460.8 | 2.869 | 419.8 | 2.886 | 420.7 |
| 3.353 | 448.7 | 3.352 | 435.2 | 3.367 | 434.9 |
| 3.835 | 439.7 | 3.834 | 449.4 | 3.777 | 446.5 |
| 4.247 | 433.3 | 4.246 | 459.2 | 4.259 | 457.1 |
| 4.725 | 426.2 | 4.724 | 468.2 | 4.738 | 465.6 |
| 5.197 | 420.1 | 5.197 | 476 | 5.214 | 472.9 |
| 5.673 | 415.3 | 5.675 | 482.4 | 5.694 | 478.8 |
| 6.148 | 411.2 | 6.146 | 488.2 | 6.165 | 484.2 |
| 6.621 | 408.5 | 6.62 | 493.9 | 6.637 | 489.2 |
| 7.094 | 406.7 | 7.095 | 499.1 | 7.111 | 493.8 |
| 7.566 | 406.3 | 7.566 | 504.4 | 7.581 | 498.7 |
| 8.036 | 406.6 | 8.038 | 509.8 | 8.051 | 503.5 |
| 8.514 | 407.8 | 8.511 | 514.7 | 8.528 | 508.3 |
| 8.977 | 409.8 | 8.979 | 519.8 | 8.991 | 512.9 |
| 9.447 | 411.9 | 9.444 | 525.1 | 9.461 | 517.8 |
| 9.932 | 414.1 | 9.916 | 530.6 | 9.934 | 522.6 |
| 9.617 | 404.7 | 9.62 | 518.4 | 9.596 | 510.5 |
| 9.141 | 395.5 | 9.149 | 504.2 | 9.137 | 496.7 |
| 8.675 | 386.4 | 8.674 | 491.3 | 8.667 | 484 |
| 8.204 | 377.6 | 8.211 | 479 | 8.19 | 471.7 |
| 7.726 | 369.2 | 7.738 | 466.6 | 7.722 | 459.4 |
| 7.267 | 360.7 | 7.269 | 454 | 7.252 | 447.1 |
| 6.789 | 352.5 | 6.796 | 441.4 | 6.778 | 434.8 |
| 6.317 | 343.6 | 6.321 | 428 | 6.309 | 421.9 |
| 5.842 | 334.7 | 5.848 | 414.3 | 5.835 | 408.5 |
| 5.366 | 325.4 | 5.375 | 400.5 | 5.355 | 394.8 |
| 4.892 | 315.4 | 4.897 | 385.6 | 4.882 | 380 |
| 4.416 | 305.2 | 4.424 | 370.2 | 4.405 | 364.8 |
| 3.932 | 294.3 | 3.943 | 353.5 | 3.927 | 348.6 |
| 3.452 | 282.3 | 3.462 | 335.3 | 3.445 | 330.7 |
| 2.969 | 269.3 | 2.977 | 315.1 | 2.962 | 311.1 |
| 2.553 | 256.6 | 2.559 | 296.1 | 2.544 | 292.4 |
| 2.059 | 239.3 | 2.068 | 270.7 | 2.048 | 267.1 |
| 1.559 | 217.8 | 1.57 | 240.5 | 1.619 | 241.6 |
| 1.116 | 193.3 | 1.131 | 208 | 1.112 | 204.9 |
| 0.6665 | 158.2 | 0.6631 | 163.5 | 0.6603 | 162 |
| 0.1976 | 95.64 | 0.1907 | 96.3 | 0.1645 | 90.64 |

TABLE 5B

Thixotropic Profiles

| Ex. 3: 1 wt % CMC, 0.06 wt % Sodium Alginate, 1.5 wt % ZnCl$_2$ | | Ex. 4: 1 wt % CMC, 0.06 wt % Sodium Alginate, 2.6 wt % Zinc Lactate | | Ex. 5: 1 wt % CMC, 0.06 wt % Sodium Alginate, 1 wt % ZnO | |
|---|---|---|---|---|---|
| Shear rate (1/s) | Shear stress (Pa) | Shear rate (1/s) | Shear stress (Pa) | Shear rate (1/s) | Shear stress (Pa) |
| 0.5192 | 179.9 | 0.5203 | 132.7 | 0.5128 | 105.8 |
| 0.9951 | 347 | 0.9945 | 256.2 | 0.9905 | 195.1 |
| 1.447 | 391.7 | 1.447 | 337.1 | 1.444 | 276.9 |
| 1.881 | 399.9 | 1.881 | 373.2 | 1.879 | 324.6 |
| 2.378 | 408.5 | 2.378 | 392.4 | 2.377 | 350 |
| 2.87 | 421.6 | 2.87 | 409.5 | 2.868 | 367.2 |
| 3.354 | 432.7 | 3.353 | 425.8 | 3.353 | 383.2 |
| 3.836 | 441.7 | 3.835 | 439.2 | 3.835 | 396.4 |
| 4.246 | 449.5 | 4.246 | 448.9 | 4.245 | 405.5 |
| 4.726 | 457.7 | 4.724 | 458.5 | 4.724 | 414 |
| 5.197 | 465.8 | 5.199 | 466.8 | 5.198 | 421 |
| 5.675 | 473.7 | 5.672 | 474.5 | 5.671 | 427.3 |
| 6.147 | 481.3 | 6.15 | 481.3 | 6.148 | 433 |
| 6.62 | 489.1 | 6.622 | 487.8 | 6.623 | 438.2 |
| 7.095 | 496.9 | 7.09 | 494.3 | 7.094 | 443.7 |
| 7.567 | 504.2 | 7.564 | 500.7 | 7.566 | 448.7 |
| 8.034 | 511.9 | 8.036 | 507 | 8.036 | 453.5 |
| 8.507 | 518.7 | 8.501 | 513.5 | 8.508 | 458.5 |
| 8.98 | 525.9 | 8.978 | 519.5 | 8.978 | 463.7 |
| 9.449 | 532.8 | 9.446 | 525.4 | 9.444 | 468.8 |
| 9.921 | 539.6 | 9.92 | 531.4 | 9.916 | 474 |
| 9.612 | 530.6 | 9.578 | 519.4 | 9.621 | 463.1 |
| 9.138 | 519.7 | 9.109 | 507.3 | 9.155 | 451.1 |
| 8.676 | 508.9 | 8.637 | 495.1 | 8.684 | 439.8 |
| 8.208 | 497.7 | 8.167 | 483 | 8.213 | 428.3 |
| 7.738 | 486.7 | 7.695 | 471.2 | 7.674 | 417 |
| 7.269 | 475.1 | 7.223 | 459 | 7.27 | 405.7 |
| 6.793 | 463.6 | 6.753 | 446.9 | 6.796 | 394.2 |
| 6.323 | 450.9 | 6.279 | 434.2 | 6.325 | 382.2 |
| 5.847 | 438.8 | 5.802 | 420.6 | 5.85 | 370.2 |
| 5.368 | 425.4 | 5.331 | 406.6 | 5.375 | 357.6 |
| 4.895 | 411.3 | 4.848 | 391.9 | 4.9 | 344.2 |
| 4.421 | 396.5 | 4.44 | 378.7 | 4.424 | 330.2 |
| 3.939 | 380 | 3.964 | 362.1 | 3.943 | 314.8 |
| 3.459 | 362.2 | 3.487 | 344.4 | 3.464 | 298.4 |
| 2.972 | 342.9 | 2.997 | 324.4 | 2.977 | 280.3 |
| 2.555 | 323.7 | 2.514 | 302.3 | 2.491 | 259.9 |
| 2.063 | 298.8 | 2.02 | 276.6 | 2.07 | 240.2 |
| 1.563 | 268.7 | 1.596 | 250.6 | 1.574 | 213 |
| 1.121 | 235.8 | 1.079 | 211.7 | 1.135 | 184.2 |
| 0.6473 | 188.6 | 0.6939 | 174 | 0.6698 | 144.9 |
| 0.2183 | 121 | 0.1865 | 98.47 | 0.2059 | 87.3 |

Antibacterial Efficacy

A Planktonic Resazurin Assay was performed on the toothpaste compositions to show their antibacterial efficacy. The results are displayed in Table 6. All five showed that the sodium zinc alginate based toothpaste compositions were significantly more antibacterial than the comparative toothpaste, which was used as a negative control (on the far right of the graph), and which did not contain any of the sodium zinc alginate structurant. Among the five sodium zinc alginate structurant formulas, zinc chloride, zinc citrate and zinc oxide/zinc citrate showed the strongest antibacterial efficacy. The zinc oxide and zinc lactate formulas were less efficacious than the first three, but were still comparable to the positive controls.

TABLE 6

Planktonic Resazurin Assay
(Toothpastes containing 1 wt % CMC, 0.06 wt % Sodium
Alginate, 0.2 wt % NaHCO$_3$, 0.8 wt % Na$_2$CO$_3$)

| Test | Zinc Compounds | Viability (%) |
|---|---|---|
| Ex. 1 | 2 wt % Zinc Citrate | 22.7 |
| Ex. 2 | 0.5 wt % Zinc Citrate, 1 wt % ZnO | 24.5 |
| Ex. 3 | 1.5 wt % ZnCl$_2$ | 19.4 |
| Ex. 4 | 2.6 wt % Zinc Lactate | 48.8 |
| Ex. 5 | 1 wt % ZnO | 36.7 |
| Positive control | 0.5 wt % Zinc Citrate, 1 wt % ZnO | 35.4 |
| Positive control | 2 wt % Zinc Citrate | 43.2 |
| C1 (Negative control) | 0 wt % Zinc Compounds, 0 wt % Sodium Alginate, 1 wt % CMC, 1 wt % MAS | 69.3 |

Thirteen-week Aging Tests

Thirteen-week accelerated aging tests were conducted on the toothpaste compositions. Table 7 through 11 show the results. It can be seen that only the toothpaste compositions using the sodium zinc oxide alginate structurant and the sodium zinc oxide/zinc citrate alginate structurant showed pH and soluble fluoride stability (see Tables 8 and 11). The other three failed the test. This indicates that over the aging period, the more soluble zinc compounds (including zinc citrate at 2 wt %), while providing good initial viscosity, had reacted with the fluoride in the composition, which resulted in producing insoluble zinc fluoride and thereby reducing the soluble fluoride (See Tables 7, 9, and 10). While not wishing to be bound to a theory, it is postulated that this is because the less soluble (thus having fewer Zn$^{2+}$ present) zinc oxide and zinc oxide/zinc citrate combinations were able to coordinate to the sodium alginates more selectively and thus kept the pH and the soluble fluoride stable throughout the aging period.

TABLE 7

Results of 13-week Aging Test for 2 wt % Zinc Citrate Formula

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| Initial Specifications | | 15-40 | A | 9.0-10.0 | 1300-1500 | 1300-1500 | 0.61-0.75 | Pass |
| Aged Specifications | | 20-70 | A | 8.8-10.0 | 1300-1500 | 1300-1500 | 0.54-0.75 | Pass |
| 25 C./60% RH | 0 mo. | 26.1 | A | 9.22 | 1335 | 1360 | 0.58 | 0, 0, 0 |
| 25 C./60% RH | 1 mo. | 46.5 | A | 8.67 | 1351 | 1347 | 0.55 | 0, 0, 0 |
| 25 C./60% RH | 2 mo. | 47.7 | A | 8.66 | 1373 | 1258 | 0.59 | 0, 0, 0 |
| 25 C./60% RH | 3 mo. | 46.9 | A | 8.75 | 1400 | 1178 | 0.59 | 0, 0, 0 |
| 40 C./75% RH | 1 mo. | 47.0 | A | 8.57 | 1349 | 1129 | 0.56 | 0, 0, 0 |
| 40 C./75% RH | 2 mo. | 44.9 | A | 8.57 | 1363 | 1012 | 0.58 | 0, 0, 0 |
| 40 C./75% RH | 3 mo. | 47.4 | A | 8.72 | 1367 | 912 | 0.59 | 0, 0, 0 |

TABLE 8

Results of 13-week Aging Test for 1 wt % Zinc Oxide and 0.5 wt % Zinc Citrate

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| Initial Specifications | | 15-40 | A | 9.0-10.0 | 1300-1500 | 1300-1500 | 0.87-1.07 | Pass |
| Aged Specifications | | 20-70 | A | 8.8-10.0 | 1300-1500 | 1300-1500 | 0.78-1.07 | Pass |
| 25 C./60 % RH | 0 mo. | 25.1 | A | 9.56 | 1336 | 1320 | 0.88 | 0, 0, 0 |
| 25 C./60 % RH | 1 mo. | 47.5 | A | 9.36 | 1355 | 1351 | 0.88 | 0, 0, 0 |
| 25 C./60 % RH | 2 mo. | 48.2 | A | 9.31 | 1399 | 1347 | 0.91 | 0, 0, 0 |
| 25 C./60 % RH | 3 mo. | 51.3 | A | 9.31 | 1391 | 1314 | 0.90 | 0, 0, 0 |
| 40 C./75 % RH | 1 mo. | 50.9 | A | 9.37 | 1382 | 1312 | 0.88 | 0, 0, 0 |

TABLE 8-continued

Results of 13-week Aging Test for 1 wt % Zinc Oxide and 0.5 wt % Zinc Citrate

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| 40 C./75 % RH | 2 mo. | 52.5 | A | 9.32 | 1375 | 1324 | 0.94 | 0, 0, 0 |
| 40 C./75 % RH | 3 mo. | 57.6 | A | 9.25 | 1392 | 1298 | 0.90 | 0, 0, 0 |

TABLE 9

Results of 13-week Aging Test for 1.5 wt % Zinc Chloride Formula

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| Initial Specifications | | 15-40 | A | 9.0-10.0 | 1300-1500 | 1300-1500 | 0.64-0.85 | Pass |
| Aged Specifications | | 20-70 | A | 8.8-10.0 | 1300-1500 | 1300-1500 | 0.64-0.85 | Pass |
| 25 C./60 % RH | 0 mo. | 25.5 | A | 8.00 | 1413 | 1004 | 0.76 | 0, 0, 0 |
| 25 C./60 % RH | 1 mo. | 48.6 | A | 8.01 | 1383 | 428 | 0.81 | 0, 0, 0 |
| 25 C./60 % RH | 2 mo. | 51.6 | A | 8.03 | 1391 | 325 | 0.74 | 0, 0, 0 |
| 25 C./60 % RH | 3 mo. | 48.5 | A | 7.90 | 1367 | 351 | 0.74 | 0, 0, 0 |
| 40 C./75 % RH | 1 mo. | 47.1 | A | 8.16 | 1378 | 149 | 0.82 | 0, 0, 0 |
| 40 C./75 % RH | 2 mo. | 49.5 | A | 8.12 | 1432 | 0 | 0.73 | 0, 0, 0 |
| 40 C./75 % RH | 3 mo. | 48.1 | A | 8.01 | 1362 | 52 | 0.72 | 0, 0, 0 |

TABLE 10

Results of 13-week Aging Test for 2.6 wt % Zinc Lactate Formula

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| Initial Specifications | | 15-40 | A | 9.0-10.0 | 1300-1500 | 1300-1500 | 0.62-0.75 | Pass |
| Aged Specificatons | | 20-70 | A | 8.8-10.0 | 1300-1500 | 1300-1500 | 0.55-0.75 | Pass |
| 25 C./60 % RH | 0 mo. | 20.0 | A | 7.76 | 1398 | 1340 | 0.68 | 0, 0, 0 |
| 25 C./60 % RH | 1 mo. | 48.3 | A | 7.70 | 1385 | 1085 | 0.67 | 0, 0, 0 |
| 25 C./60 % RH | 2 mo. | 51.4 | A | 7.65 | 1397 | 981 | 0.61 | 0, 0, 0 |
| 25 C./60 % RH | 3 mo. | 50.6 | A | 7.70 | 1364 | 923 | 0.60 | 0, 0, 0 |
| 40 C./75 % RH | 1 mo. | 48.1 | A | 7.79 | 1390 | 706 | 0.67 | 0, 0, 0 |
| 40 C./75 % RH | 2 mo. | 46.7 | A | 7.84 | 1414 | 385 | 0.60 | 0, 0, 0 |
| 40 C./75 % RH | 3 mo. | 44.6 | A | 7.91 | 1219 | 292 | 0.60 | 0, 0, 0 |

TABLE 11

Results of 13-week Aging Test for 1 wt % Zinc Oxide Formula

| Cond. | Time | Viscosity (x 10000 cps) | physical exam | pH (20% sol.) | Total Fluoride (ppm) | Soluble Fluoride (ppm) | Total Zinc (%) | Liquid Sep. |
|---|---|---|---|---|---|---|---|---|
| Initial Specifications | | 15-40 | A | 9.0-10.0 | 1300-1500 | 1300-1500 | 0.72-0.88 | Pass |
| Aged Specificatons | | 20-70 | A | 8.8-10.0 | 1300-1500 | 1300-1500 | 0.64-0.88 | Pass |
| 25 C./60 % RH | 0 mo. | 22.4 | A | 10.04 | 1419 | 1312 | 0.85 | 0, 0, 0 |
| 25 C./60 % RH | 1 mo. | 46.2 | A | 9.89 | 1408 | 1394 | 0.81 | 0, 0, 0 |
| 25 C./60 % RH | 2 mo. | 45.9 | A | 9.81 | 1381 | 1382 | 0.80 | 0, 0, 0 |
| 25 C./60 % RH | 3 mo. | 46.0 | A | 9.78 | 1374 | 1417 | 0.83 | 0, 0, 0 |
| 40 C./75 % RH | 1 mo. | 50.4 | A | 9.83 | 1411 | 1401 | 0.85 | 0, 0, 0 |
| 40 C./75 % RH | 2 mo. | 48.3 | A | 9.76 | 1399 | 1328 | 0.79 | 0, 0, 0 |
| 40 C./75 % RH | 3 mo. | 46.0 | A | 9.81 | 1389 | 1416 | 0.82 | 0, 0, 0 |

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. It should also be appreciated that the numerical limits may be the values from the examples. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A method of making a sodium zinc alginate structurant comprising:
    combining a sodium alginate, a zinc compound, and a liquid media; and
    mixing the sodium alginate, the zinc compound, and the liquid media to make a sodium zinc alginate structurant,
    wherein combining comprises combining the sodium alginate and the zinc compound in a weight ratio of about 0.04:1,
    wherein the zinc compound comprises zinc oxide and zinc citrate in a weight ratio of about 2:1, and
    wherein the sodium zinc alginate structurant has a viscosity of about 1,200 cP to about 2,000 cP at 25° C.

2. The method of claim 1, wherein combining comprises combining the sodium alginate and the zinc compound in an amount from about a 0.8 wt % to about 1.2 wt %, based on the total weight of the sodium alginate, the zinc compound, and the liquid media, and wherein the liquid media comprises water.

3. A method of making an oral care composition comprising:
    combining a sodium alginate, a zinc compound, and a liquid media;
    mixing the sodium alginate, the zinc compound, and the liquid media to make a sodium zinc alginate structurant; combining the sodium zinc alginate structurant with one or more agents; and
    mixing the sodium zinc alginate structurant with one or more agents to make the oral care composition,
    wherein combining comprises combining the sodium alginate and the zinc compound in a weight ratio of about 0.04:1,
    wherein the zinc compound comprises zinc oxide and zinc citrate in a weight ratio of about 2:1, and
    wherein the sodium zinc alginate structurant has a viscosity of about 1,200 cP to about 2,000 cP at 25° C.

4. The method of claim 3, wherein combining comprises combining the sodium alginate and the zinc compound in an amount from about a 0.8 wt % to about 1.2 wt %, based on the total weight of the sodium alginate, the zinc compound, and the liquid media, and wherein the liquid media comprises water.

* * * * *